Figure 1:
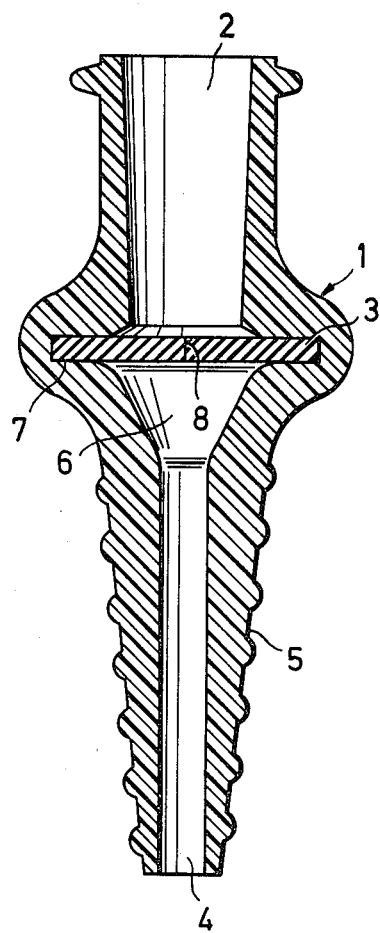

United States Patent [19]

Tauschinski

[11] 4,387,879
[45] Jun. 14, 1983

[54] SELF-SEALING CONNECTOR FOR USE WITH PLASTIC CANNULAS AND VESSEL CATHETERS

[75] Inventor: Stefan Tauschinski, Vienna, Austria

[73] Assignee: Eduard Fresenius Chemisch Pharmazeutische Industrie KG, Bad Homburg von der Hohe, Fed. Rep. of Germany

[21] Appl. No.: 284,136

[22] Filed: Jul. 16, 1981

Related U.S. Application Data

[63] Continuation of Ser. No. 30,390, Apr. 16, 1979.

[30] Foreign Application Priority Data

Apr. 19, 1978 [DE] Fed. Rep. of Germany ....... 2817102

[51] Int. Cl.³ .......................................... F16K 37/28
[52] U.S. Cl. ................................ 251/149.1; 137/846; 604/247; 604/249
[58] Field of Search ............ 128/214 R, 214 G, 214.2, 128/221, 247, 274; 137/845, 846; 251/149.1, 149.4, 331; 604/247, 249

[56] References Cited

U.S. PATENT DOCUMENTS

| 962,027 | 6/1910 | Kennedy | 137/846 X |
| 3,570,484 | 3/1971 | Steer | 128/274 X |
| 3,601,151 | 8/1971 | Winnard | 137/846 |
| 3,620,500 | 11/1971 | Santomieri | 251/149.1 |
| 3,848,579 | 11/1974 | Villa-Real | 128/218 NV |
| 4,143,853 | 3/1979 | Abramson | 251/149.1 |

*Primary Examiner*—Dalton L. Truluck
*Attorney, Agent, or Firm*—Perry Carvellas

[57] ABSTRACT

A connector which is adapted to be connected to a plastic cannula or a vein catheter comprises a tubular and/or conical portion that is adapted to be tightly joined to a parenteral solution supply needle and/or to a hose provided with a cone fitting. To ensure that a metal cannula or a vessel catheter can be pushed through the connector without obstruction and that the connector closes automatically as soon as the metal cannula or the catheter or the cone fitting of a supply hose has been pulled from the connector, the body of the latter is provided with a receptable, which is radial with respect to the flow passage, and a disc consisting of elastomeric material and having a central slit is held in said receptacle and blocks the flow passage.

11 Claims, 4 Drawing Figures

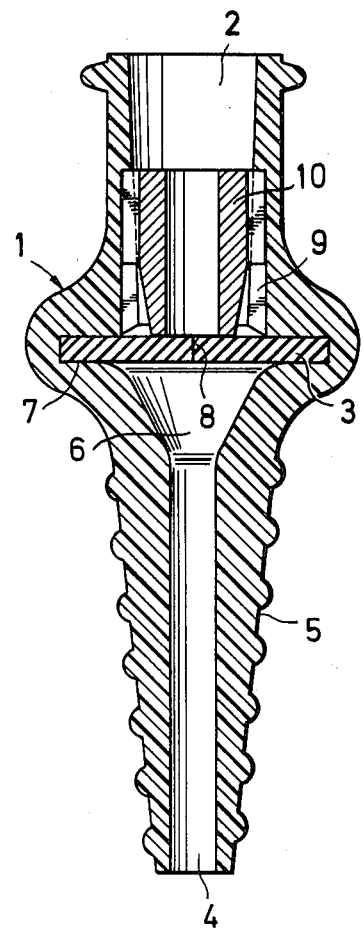
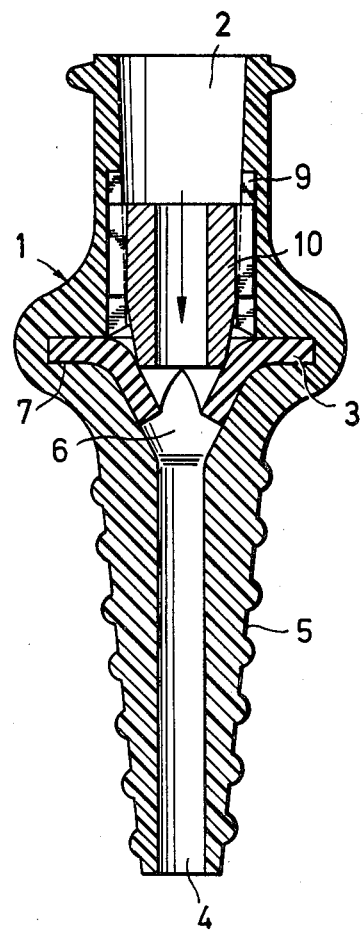

U.S. Patent   Jun. 14, 1983   Sheet 3 of 3   4,387,879

SELF-SEALING CONNECTOR FOR USE WITH PLASTIC CANNULAS AND VESSEL CATHETERS

This is a continuation of application Ser. No. 030,390 filed Apr. 16, 1979.

This invention relates to a connector which is adapted to be connected to a plastic cannula or a vein catheter and comprises a tubular and/or conical portion that is adapted to be tightly joined to a parenteral solution supply needle and/or to a hose provided with a cone fitting.

Plastic cannulas and vein catheters are used in medicine to supply blood or parenteral solution into the vessel system of patients. The plastic cannula or a short catheter contains a sharp metal cannula and by means of the latter is pierced through the skin and the tissue and introduced into a blood vessel. Through a plastic cannula which has been applied, a long catheter can be introduced into the vessel system. If a peripheral vein is to be punctured the same is squeezed off on its distal side and is thus caused to swell to a larger volume. When the vein has been punctured the metal needle is removed from the plastic cannula. In that operation it has hardly been possible before to prevent an emergence of blood from the cone fitting which was connected to the cannula. When a short catheter is introduced by means of an internally disposed needle into a large vena cava and is subsequently advanced as far as to the vena cava superior, an emergence of blood from the cone fitting cannot be prevented even when the patient is properly placed. If the patient is improperly placed or when he makes spontaneous movements or coughs, there is an additional danger that a vacuum may occur in the punctured vena cava so that air is sucked through the catheter. This may result in air embolism.

In another method of vein catheterizing, the bore of the catheter is sealed by a core and the catheter is introduced through a plastic cannula, which has previously been introduced into the vein. In that method an emergence of blood from the cannula and from the catheter when the sealing core has been removed can hardly be avoided.

A special danger resides in that the supply hose for the parenteral solution may inadvertently detach from the cone fitting of the vein catheter. When a subclavian catheter is applied to a seated patient, for instance, this may result in air embolism. On the other hand, blood would continually emerge from a peripheral catheter or the latter would be clogged by coagulation.

The emergence of blood from the cone fitting of cannulas and catheters had previously to be put up with although it may have most serious consequences particularly in long-term treatments. For instance, mass examinations of vessel catheters have shown that a high percentage of the catheters was infected with bacteria.

In that finding it was most remarkable that in most cases the infection had been effected at the tip of the catheter rather than at the point where the catheter emerged from the skin. This suggests that the bacteria had grown through the catheter, which was contaminated with blood, and had thus entered the interior of the catheter and accumulated at its tip.

It has been attempted to prevent an emergence of blood and a risk of an entrance of air into the vein by the provision of a two-way of three-way cock between the cannula or catheter, on the one hand, and the cone fitting, on the other hand. But because the physician must use both hands in handling the plastic cannula or the catheter, a helper is required for turning the cock to its closed position. Besides, the cock must be closed very promptly because blood will otherwise enter the fitting. And even such cock cannot prevent an inadvertent detaching of the hose from the catheter.

For this reason it is an object of the present invention to provide a connector which is of the kind mentioned first hereinbefore and through which a metal cannula or a vessel catheter can be pushed without obstruction but which will close automatically as soon as the metal cannula or the catheter or the cone fitting of a supply hose has been pulled from such connector. The connector is intended to close as the metal cannula, the vessel catheter or the cone fitting of the supply hose are pulled out of the fitting or inadvertently fall from the same, and the closed connector is intended to prevent an emergence of blood or an ingress of air through the fitting.

This object is accomplished according to the invention in that the body of the connector is provided with a receptacle, which is radial with respect to the flow passage, and a disc consisting of electromeric material and having a central slit is held in said receptacle and blocks the flow passage. The slit may be straight or Y-shaped or star-shaped. A metal cannula or a catheter hose can be inserted through the central slit of the rubber-elastic, plane disc of the connector according to the invention, and when the cannula or hose has been pulled out the slit is tightly closed to seal the passage, owing to the elasticity of the disc. In consideration of the diameter, the thickness and the material of the disc, the length of the slit is selected so that metal cannulas and catheter hoses can properly be pushed through the slit and that a tight seal is ensured when such cannula or hose has been removed.

The disc may be circular and is suitably larger than its receptacle so that the disc is force-fitted in the receptacle and applies to the periphery of the receptacle a pressure which improves the seal at the slit.

According to a preferred further feature of the invention, a member having a central through hole is guided in the conical entrance passage of the connector body and is longitudinally slidable within limits to such an extent that when the member is retracted its forward end face is clear of the flat disc and when the member is advanced it protrudes at least through part of the disc to open the slit. If the connector body has a hollow-conical extension and a cone fitting, e.g., of a supply hose, is pushed into said extension, the cone fitting will advance the longitudinally slidable member toward the disc to open the slit and to lock said member in position. When the cone fitting of the supply hose is pulled out or falls off inadvertently, the elastically deformed disc will urge the member back so that the slit closes tightly.

Further desirable embodiments of the invention will be defined more in detail in the sub-claims.

All illustrative embodiment of the invention will now be explained more fully with reference to the accompanying drawing, in which FIG. 1 is a longitudinal sectional view showing on an enlarged scale a connector provided with a slit sealing disc, FIG. 2 is a view similar to FIG. 1 and shows a connector having an axially slidable, central member, and FIG. 3 shows the connector of FIG. 2 with the member advanced to open the slit in the disc.

Figure 4:
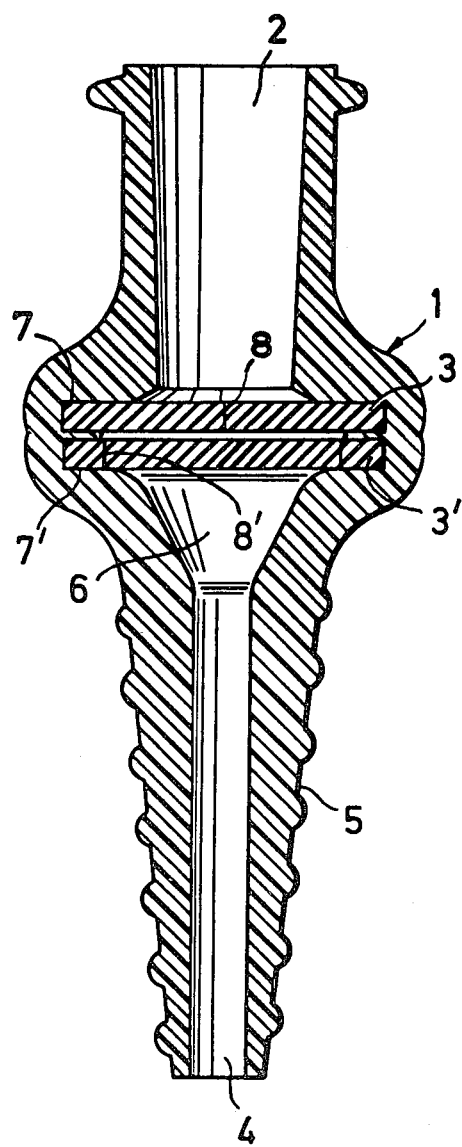

FIG. 4 shows the connector of FIG. 1 with two adjoining elastomeric discs having their central slits cross each other.

A plastic connector body shown in FIG. 1 has at its entrance and a hollow-conical portion 2, which can be tightly connected to an inserted fitting cone of a hose for supplying a parenteral solution. The connector body 1 is provided at its exit end with a cylindrical passage 4, which has a diameter that has been selected in view of the diameter of a cannula or catheter which can be inserted. That portion of the connector body which surrounds the passage 4 is conically tapered and provided with peripheral annular ribs and serves to retain a hose, which leads to the vessel system. A chamber 6 connects the interior of the hollow-conical portion 2 to the passage 4 and is provided with a peripheral annular radial groove 7, in which a disc 3 of elastic material is held. The disc 3 is provided with a central slit 8, which terminates short of the edge of the disc.

The embodiment shown in FIGS. 2 and 3 differs from the embodiment shown in FIG. 1 in that the inside surface of the hollow-conical portion 2 is formed with two or more axial guide grooves 9, which are engaged by mating splines of a member 10, which is axially slidable between limits. Alternatively, the cylindrical portion of the member 10 may be guided in a mating cylindrical bore. The member 10 has a central through bore and has a square rear end face whereas its forward end portion is frustoconical. In the position shown in FIG. 2 the forward end of the member 10 just contacts the disc 3, which has sprung back to its plane position, so that the slit 8 of the disc 3 is tightly closed.

In FIG. 3 the member 10 is shown in a position to which it has been advanced by a oval fitting, not shown, of a supply hose. In that position the slit 8 is open because it has been expanded.

Instead of one slit disc of elastomeric material, two or more adjoining discs may be provided, which have central slits crossing each other. When two discs are provided, the crossing slits may extend at an angle of 90° to each other. When three discs are provided, adjacent slits include an angle of 60°.

FIG. 4 there is shown peripheral annular radial groove 7' in which 3' is provided with a central slit 8', which terminates a short distance short of the edge of the disc.

The slidable member 10 need not be guided in grooves but may have a cylindrical outside surface, provided that suitable means are provided to prevent the member 10 from falling out of the connector 1.

To ensure that the member 10 is easily slidable, ribs which are preferably semicircular in cross-section may be provided on the inside surface of the hollow-conical portion 2 or on the peripheral surface of the slidable member 10. The member 10 does not only open the slit 8 in the disc 3 but reduces also the friction between the disc 3 and the inserted element, which may consist of a cannula, a catheter, or a core for a catheter.

What is claimed is:

1. A connector consisting essentially of a hollow longitudinal passage, a hollow body portion containing a chamber, a hollow inlet portion and a hollow outlet portion, said connector containing a longitudinally slidable member, having a central opening, disposed within said longitudinal passage, and slidable within limits in said longitudinal passage, said member contacting and cooperating with a deformable elastomeric disc, having a central slit, disposed and held in place within the chamber of said body portion transversely across said longitudinal passage to close off the passage, said inlet portion having a hollow conical portion adapted to be connected to a parenteral solution supply needle or hose having a cone fitting, said outlet portion having a hollow passage and being adapted to be connected to a cannula, catheter or hose; said longitudinally slidable member cooperating with said cone fitting such that when said cone fitting is inserted into said inlet hollow conical portion the cone fitting contacts and causes the longitudinal slidable member to advance and protrude at least through part of the elastomeric disc to open the slit in the disc and provide communication between the hollow inlet portion, the chamber in the body portion and the hollow outlet portion, the elastomeric disc providing resilient means such that when the cone fitting is withdrawn from the inlet portion of the connector the disc springs back to its original position closing the slit and sealing the disc and thereby forceably urging the longitudinally slidable member to retract to its original position.

2. The connector of claim 1 wherein the elastomeric disc is circular.

3. The connector of claim 1 wherein the disc is force-fitted across the chamber in the body portin of the connector.

4. The connector of claim 1 wherein the elastomeric disc is disposed in the chamber of the body portion of the connector which joins the inlet portion to the outlet portion of the connector.

5. The connector of claim 1 wherein the slidable member has a frusto conical shape forward end portion.

6. The connector of claim 1 wherein the chamber of the body portion when viewed in the direction of flow is conically tapered.

7. The connector of claim 1 wherein two or more adjoining elastomeric discs are provided and their central slits cross each other.

8. The connector of claim 1 wherein the slit in the elastomeric disc is straight, Y-shaped or star-shaped.

9. The connector of claim 1 wherein the slidable member has a cylindrical portion which is guided in a mating bore that is formed in the connector body and is larger in axial length.

10. The connector of claim 1 wherein the slidable member has axially extending splines, semicircular-sections or ribs which engage mating guide grooves in the connector body.

11. The connector of claim 1 wherein the splines, semicircular-sections or ribs and mating guide grooves prevent the slidable member from falling out of the connector body.

* * * * *